United States Patent [19]

Pyrz et al.

[11] Patent Number: 4,847,070

[45] Date of Patent: Jul. 11, 1989

[54] ANTICALCULUS COMPOSITIONS

[75] Inventors: Joseph W. Pyrz; Anthony C. Lanzalaco, both of Fairfield; Richard J. Sunberg, Oxford, all of Ohio

[73] Assignee: The Procter & Gamble Company, Cincinnati, Ohio

[21] Appl. No.: 106,198

[22] Filed: Oct. 8, 1987

[51] Int. Cl.$^4$ .......................... A61K 7/18; A61K 7/16
[52] U.S. Cl. ........................................ 424/52; 424/48; 424/49; 424/57; 424/464; 514/901
[58] Field of Search ................... 424/48–49, 424/52, 57, 464; 514/901

[56] References Cited

U.S. PATENT DOCUMENTS

| | | | |
|---|---|---|---|
| 3,429,963 | 2/1969 | Shedlovsky | 424/56 |
| 3,956,480 | 5/1976 | Dichter | 424/54 |
| 3,988,434 | 10/1976 | Schole et al. | 424/54 |
| 4,175,120 | 11/1979 | Schole | 424/54 |
| 4,224,310 | 9/1980 | Shah | 424/54 |
| 4,323,551 | 4/1982 | Parran Jr. | 424/54 |
| 4,367,219 | 1/1983 | Schole | 424/52 |
| 4,415,549 | 11/1983 | Shah et al. | 424/52 |

FOREIGN PATENT DOCUMENTS 0079611 6/1983 European Pat. Off. .

*Primary Examiner*—Delbert R. Phillips
*Assistant Examiner*—F. T. Moezie
*Attorney, Agent, or Firm*—Richard C. Witte; Jack D. Schaeffer; Douglas C. Mohl

[57] ABSTRACT

Disclosed are oral compositions which are effective against calculus and contain a chelating agent which is an acrylic acid polymer or copolymer or EDTA, a strontium ion source, a fluoride ion source and a pyrophosphate ion source.

22 Claims, No Drawings

ANTICALCULUS COMPOSITIONS

TECHNICAL FIELD

The present invention relates to oral compositions which provide anticalculus benefits.

BACKGROUND OF THE INVENTION

Dental calculus, or tartar as it is sometimes called, is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic portion which is largely calcium phosphate arranged in a hydroxyapatite crystal lattice structure similar to bone, enamel and dentine. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. This is undesirable from an aesthetic standpoint.

A wide variety of chemical and biological agents have been suggested in the art to retard calculus formation or to remove calculus after it is formed. Mechanical removal of this material periodically by the dentist is, for course, routine dental office procedure.

The chemical approach to calculus inhibition generally involves chelation of calcium ion and/or crystal growth inhibition which prevents the calculus from forming and/or breaks down mature calculus by removing calcium.

The prior art discloses a number of chelating agents for this purpose. British Pat. No. 490,384, Feb. 15, 1937, discloses oral compositions containing ethylenediaminetetraacetic acid, nitrilotriacetic acid and related compounds as anticalculus agents. U.S. Pat. No. 3,678,154, July 18, 1972 to Widder et al. discloses oral compositions containing certain polyphosphonates and fluoride. U.S. Pat. No. 3,737,533, June 5, 1973 to Francis discloses oral compositions containing certain carbonyl diphosphonates.

In addition to the above references, the prior art discloses dentifrices and mouthwashes containing soluble pyrophosphate salts which have been included for a variety of purposes. Included among such references are U.S. Pat. No. 2,941,926, June 21, 1960 to Salzmann et al. which discloses dental powders containing chlorophyll and pyrophosphate salts. U.S. Pat. No. 3,137,632, June 16, 1964 to Schiraldi discloses toothpastes containing pyrophosphate salts. U.S. Pat. Nos. 3,927,201 and 3,927,202, Dec. 16, 1975 to Baines et al. and Harvey et al., respectively, disclose toothpastes which utilize soluble pyrophosphates as abrasives. U.S. Pat. Nos. 4,244,931, Jan. 13, 1981 and 4,247,526, Jan. 27, 1981 to Jarvis et al. disclose pyrophosphate salts in dicalcium phosphate systems. Japanese Patent Application Disclosure No. 4945-1974 discloses soluble pyrophosphates in a variety of dentifrice systems. U.S. Pat. No. 4,323,551, Apr. 6, 1982 to Parran discloses tetraalkali metal salts in mouthwash compositions.

In addition to the use of the above mentioned materials the use of certain acrylic acid polymers and other agents have also been disclosed for use as anticalculus agents. Included among such agents are polyelectrolytes such as copolymers of maleic anhydride and ethylene disclosed in U.S. Pat. No. 3,429,963, Feb. 25, 1969 to Shedlovsky. Shedlovsky also discloses polyacrylic acid having an average molecular weight of 1500 and greater. Other references disclosing polyacrylic acids in oral compositions are South African Pat. No. 720898, Sept. 12, 1972 which discloses such acids having a molecular weight of from 1000 to 2,000,000; and U.S. Pat. No. 4,304,766, Dec. 8, 1971 to Chang discloses polyacrylic acid having a molecular weight in the range of 2,000 to 4,000,000 for use as a membrane to prevent the elution from teeth of previously applied agents. Finally, U.S. Pat. No. 3,956,480, May 11, 1976 discloses complexes of anionic polymers (e.g., acrylic acid) and a cationic therapeutic agent (e.g., chlorhexidine) as anticalculus agents.

In addition to the above described materials, strontium edadate has been disclosed in dentifrice compositions for use in controlling calculus. One reference having such a disclosure is U.S. Pat. No. Re. 30,675, July 14, 1981.

In spite of the many disclosures in the anticalculus area, the need for improved anticalculus products still exist. The prior art, while disclosing strontium complexes and pyrophosphate salts as anticalculus agents, does not teach or suggest the combining of such agents to achieve an enhanced benefit.

It is an object of the present invention to provide compositions which deliver an effective anticalculus benefit.

It is a further object of the present invention to provide an effective anticalculus product utilizing polyacrylic acid polymers or copolymers having a mass average molecular weight of from about 3500 to about 7500.

It is a further object of the present invention to provide an anticalculus product which does not inhibit remineralization of the teeth.

It is still a further object of the present invention to provide an effective method for treating calculus.

It is still a further object of the present invention to provide compositions which are cosmetically acceptable.

These and other objects will become more clear from the detailed description which follows.

All percentages and ratios used herein are by weight unless otherwise specified. Also all measurements referred to herein are made at 25° C. in the composition unless otherwise specified.

SUMMARY OF THE INVENTION

The present invention embraces oral compositions comprising:
 (a) a safe and effective amount of a chelating agent selected from the group consisting of polyacrylic acid polymers or copolymers, EDTA, EDTA analogues and mixtures thereof;
 (b) a safe and effective amount of a strontium ion source;
 (c) a safe and effective amount of a soluble pyrophosphate ion source;
 (d) a safe and effective amount of a fluoride ion source; and
 (e) a pharmaceutically acceptable carrier.

The present invention also encompasses a method for retarding the development of calculus.

DETAILED DESCRIPTION OF THE INVENTION

The compositions of the present invention comprise polyacrylic acid polymers or copolymers or EDTA, a strontium ion source, a pyrophosphate ion source, a fluoride ion source and a pharmaceutically acceptable carrier.

By "oral compositions" as used herein means a product which in the ordinary course of usage is not intentionally swallowed for purposes of systemic administration of particular therapeutic agents, but is rather retained in the oral cavity for a time sufficient to contact substantially all the dental surfaces and/or oral tissues for purposes of oral activity.

By "safe and effective amount" as used herein means sufficient amount of material to provide the desired benefit while being safe to the hard and soft tissues of the oral cavity.

By the term "comprising", as used herein, is meant that various additional components can be conjointly employed in the compositions of this invention as long as the listed materials perform their intended functions.

By the term "carrier, as used herein, is meant a suitable vehicle which is pharmaceutically acceptable and can be used to apply the present compositions in the oral cavity.

Polyacrylic Acid Polymers - EDTA

The polyacrylic acid polymers are staple items of commerce and are made by polymerizing acrylic acid,

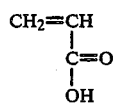

to for the repeating chain

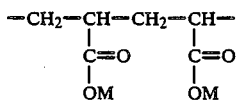

wherein M is an alkali metal, ammonium or hydrogen ion. Polymers of the type useful in the present invention are available from Rohm and Haas Company.

Copolymers of acrylic acid and other monomers may also be used in the present invention. Suitable other monomers include methacrylic acid, 2-hydroxypropyl acrylate, 3-hydroxypropyl methacrylate, 3-hydroxy propyl acrylate and acrylamide. It is preferred that with methacrylic acid, the number of acrylic acid units in the polymer be at least 50% of the total units present. With other monomers it is preferred that the percentage be at least 80%. Mixtures of other monomers may also be used.

The molecular weight of the polymer may be in the range of about 1000 to about 1,200,000 (mass average), preferably the molecular weight is from about 3500 to about 7500, most preferably from about 4300 to about 5200. A particularly preferred material is a polyacrylic acid polymer having a molecular weight of about 4500 which can be provided by Rohm and Haas carrying the identification LMW-45. It is to be appreciated that mixtures of high molecular weight materials and lower molecular weight materials may be used to achieve a polymer mixture having an appropriate mass average molecular weight.

The amount of the polymer used in the present compositions is generally from about 0.0003% to about 13%, preferably from about 0.03% to about 5%, most preferably from about 0.03% to about 3.0%. For a dentifrice composition containing about 2200 ppm $Sr^{++}$ the preferred level of polymer is from about 0.3% to about 1.0%. For a mouthwash composition containing about 450 ppm $Sr^{++}$ the preferred polymer level is from about 0.03% to about 1.0%. Mixtures of polyacrylic acid polymers or copolymers are also useful in the present invention.

Another chelator useful in the present compositions, used alone or in combination with the polyacrylic acid polymer is EDTA. This material, if present, is used at a level of from about 0.4% to about 1.4%, preferably from about 0.4% to about 0.8% expressed as the disodium salt. The amount used should preferably be an equal molar amount with the amount of the $Sr^{++}$ ion.

Strontium Ion Source

The strontium ions of the present compositions can be provided by any of a wide variety of strontium salts or complexes. Included are strontium chloride, strontium acetate, strontium bromide, strontium glyconate, strontium lactate, strontium hydroxide and strontium salicylate. In another execution strontium can be provided to the present compositions as a complex with the polyacrylic acid or EDTA. The strontium ion source is soluble enough in the composition at 25° C. or when used to provide from about 2 to about 10,000, preferably from about 25 to about 4400 ppm $Sr^{++}$.

Pyrophosphate Salts

The pyrophosphate salt used in the present compositions can be any of the alkali metal pyrophosphate salts. Specific salts include tetra alkali metal pyrophosphate, dialkali metal diacid pyrophosphate, trialkali metal monoacid pyrophosphate and mixtures thereof, wherein the alkali metals are preferably sodium or potassium. The salts are useful in both their hydrated and unhydrated forms. The amount of pyrophosphate salt useful in the present composition is any effective amount and is preferably enough to provide at least 1.0% $P_2O_7^{-4}$, preferably from about 1.5% to about 6%, to the compositions. It is to be appreciatd that the level of $P_2O_7^{-4}$ is that capable of being provided to the composition (i.e., the theoretical amount at an appropriate pH) and that other pyrophosphate forms (e.g., $HP_2O_7^{-3}$) may be present when a final product pH is established.

The pyrophosphate salts are described in more detail in Kirk & Othmer, *Encyclopedia of Chemical Technology*, Second Edition, Volume 15, Interscience Publishers (1968), incorporated herein by reference.

Preferred pyrophosphate salts for use herein are tetrasodium pyrophosphate, tetrapotassium pyrophosphate, mixtures of tetrapotassium and tetrasodium pyrophosphates, mixtures of diakalimetal pyrophosphate salts with one or both of the tetra salts and diakalimetal salts alone. The latter two systems are preferred.

Fluoride Ion Source

The water-soluble fluoride compound is present in the compositions of this invention in an amount sufficient to give a fluoride concentration of from about 0.0025% to about 5.0% by weight, preferably from about 0.005% to about 2.0% by weight of 25° C., in the composition or when used to provide anticaries effectiveness. Preferred fluorides are sodium fluoride, stannous fluoride, indium fluoride, acidulated phosphate fluoride and sodium monofluorophosphate. U.S. Pat. No. 2,946,735, July 26, 1960 to Norris et al. and U.S. Pat. No. 3,678,154, July 18, 1972 to Widder et al. disclose such salts as well as others. These references are incorporated herein by reference.

Pharmaceutically Acceptable Carrier

The carrier for the components of the present invention can be any vehicle suitable for use in the oral cavity. Such carriers include the usual components of mouthwashes, toothpastes, topical dental gels, toothpowders, prophylaxis pastes, lozenges, gums and the like and are more fully described hereinafter. Dentifrices and mouthwashes are the preferred systems with toothphastes being the more preferred.

Toothpastes and toothpowders contain as a major component an abrasive. The abrasive polishing material contemplated for use in the present invention can be any material which does not excessively abrade dentin. These include, for example, silicas including gels and precipitates, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al, in U.S. Pat. No. 3,070,510, Dec. 25, 1962, incorporated herein by reference. Mixtures of abrasives may also be used.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride and other ion sources. For these reasons they are preferred for use herein. Of course the abrasive selected should also exhibit excellent compatibility with soluble strontium ion sources.

The silica abrasive polishing materials useful herein, as well as the other abrasives, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, June 21, 1975, both incorporated herein by reference. Preferred are the silica xerogels marketed under the tradename "Syloid" by the W.R. Grace & Company, Davison Chemical Division. Preferred precipitated silica materials include those marketed by the J.M. Humber Corporation under the tradename, "Zeodent", particularly the silica carrying the designation "Zeodent 119". These silica abrasive are described in U.S. Patent No. 4,340,583, July 29, 1982, incorporated herein by reference.

The abrasive in the dentifrice compositions described herein is present at a level of from about 6% to about 70%, preferably from about 15% to about 25% when the dentifrice is a toothpaste. Higher levels, as high as 90%, may be used if the composition is a toothpowder.

Flavoring agents can also be added to the dentifrice and other compositions of the present invention. Suitable flavoring agents include oil of wintergreen, oil of peppermint, oil of spearmint, oil of sassafras, and oil of clove. Sweetening agents are also useful and include aspartame, acesulfame, saccharin, dextrose, levulose and sodium cyclamate. Flavoring and sweetening agents are generally used in the compositions herein at levels of from about 0.005% to about 2% by weight.

The compositions of this invention also contain emulsifying agents. Suitable emulsifying agents are those which are reasonably stable and foam throughout a wide pH range, including non-soap anionic, nonionic, cationic, zwitterionic and amphoteric organic synthetic detergents. Many of these suitable surfactants are disclosed by Gieske et al. in U.S. Pat. No. 4,051,234, Sept. 27, 1977 incorporated herein by reference.

Water is also present in the compositions of this invention. Water employed in the preparation of commercially suitable compositions should preferably be deionized and free of organic impurities. Water generally comprises from about 10% to 50%, preferably from about 20% to 40%, by weight of the toothpaste compositions herein. These amounts of water include the free water which is added plus that which is introduced with other materials such as with sorbitol.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic, and gum tragacanth and polysaccharide gums such as xanthan gum can also be used. Colloidal magnesium aluminum silicate or finely divided silica can be used as part of the thickening agent to further improve texture. Thickening agents in an amount from 0.5% to 5.0% by weight of the total composition may be used.

It is also desirable to include a humectant in a toothpaste to keep it from hardening. Suitable humectants include glycerin, sorbitol, and other edible polyhydric alcohols at a level of from about 10% to about 70%.

Another preferred embodiment of the present invention is a mouthwash composition. Conventional mouthwash composition components can comprise the carrier for the actives of the present invention. Mouthwashes generally comprise from about 20:1 to about 2:1 of a water/ethyl alcohol solution and preferably other ingredients such as flavor, sweeteners, humectants and sudsing agents such as those described above. The humectants, such as glycerin and sorbitol give a moist feel to the mouth. Generally, on a weight basis the mouthwashes of the invention comprise 5% to 60% (preferably 10% to 25%) ethyl alcohol, 0% to 20% (preferably 5% to 20%) of a humectant, 0% to 2% (preferably 0.01% to 0.15%) emulsifying agent, 0% to 0.5% (preferably 0.005% to 0.06%) sweetening agent such as saccharin, 0% to 0.3% (preferably from 0.03% to 0.3%) flavoring agent, and the balance water.

Suitable lozenge and chewing gum components are disclosed in U.S. Pat. No. 4,083,955, Apr. 11, 1978 to Grabenstetter et al., incorporated herein by reference.

Suitable topical dental gels generally comprise a base of a humectant such as glycerine thickened with a suitable agent. Such gels generally do not contain an abrasive.

The pH of the present compositions and/or its pH in the mouth can be any pH which is safe from the mouth's hard and soft tissues. Such pH's are generally from about 3 to about 10, preferably from about 4 to about 9. The present compositions, since they are designed to deliver an anticalculus benefit should not contain materials which would cause significant loss of the necessary ions.

METHOD OF MANUFACTURE

The carrier compositions of the present invention can be made using methods which are common in the oral products area. However the strontium ion source and the polyacrylic acid polymer should be added prior to the addition of the fluoride ion source. This is to ensure that strontium and fluoride do not form an insoluble precipitate. A specific method of manufacture is set forth in the Examples.

EXAMPLES I-IV

The following are representative compositions of the present invention.

| Component | Weight % | | | |
| --- | --- | --- | --- | --- |
| | I | II | III | IV |
| Sodium Fluoride (ppm active) | 0.243 (1100) | 0.243 (1100) | 0.243 (1100) | 0.243 (1100) |
| Sr(OH)2 (ppm active) | 0.667 (2200) | 0.667 (2200) | 0.667 (2200) | 0.667 (2200) |
| Polyacrylic acid (% active) | 1.923 (0.75%) | — | — | 1.923 (0.75%) |
| EDTA Disodium Salt (% active) | — | 0.935 (0.65%) | 0.935 (0.65%) | — |
| Saccharin | 0.280 | 0.280 | 0.286 | 0.286 |
| Sorbitol | 30.0 | 30.0 | 30.4 | 30.4 |
| Silica | 24.0 | 24.0 | 22.0 | 22.0 |
| Tetrasodium pyrophosphate | 3.40 | 3.40 | 3.58 | 3.58 |
| Sodium acid pyrophosphate | 1.37 | 1.37 | 1.22 | 1.22 |
| Xanthan gum | 0.80 | 0.80 | — | — |
| Carbopol - 941[1] | 0.25 | 0.25 | 0.35 | 0.35 |
| Carrageenan | — | — | 0.55 | 0.55 |
| Polyethylene Glycol-300 | 5.00 | 5.00 | — | — |
| Polyethylene Glycol-6 | — | — | 1.00 | 1.00 |
| Sodium alkyl sulfate (27% aqueous solution) | 5.00 | 5.00 | 4.00 | 4.00 |
| TiO2 | 0.525 | 0.525 | 0.525 | 0.525 |
| Flavor | 1.044 | 1.044 | 1.044 | 1.044 |
| Color | 0.050 | 0.050 | 0.050 | 0.050 |
| NaOH to pH | 7.5 | 7.5 | 7.5 | 7.5 |
| Water q.s. to | 100% | 100% | 100% | 100% |

[1] A carboxyvinyl polymer sold by B. F. Goodrich Company.

The above compositions are prepared by putting approximately 20% of the sorbitol and 15% of the water into a slurry tank, adding all of the polyacrylic acid and mixing for a few minutes. Strontium hydroxide is then added and dissolved in the slurry tank with the desired pH being obtained by adding HCl or NaOH. Sodium fluoride and sodium saccharin are dissolved in water and added to the slurry tank. This mixture is added to the main mix tank, with additionl sorbitol and water, followed by titanium dioxide, dye, pyrophosphates, and silica abrasive. The binders are then dispersed in polyethylene glycol or sorbitol and added to the main mix tank followed by the surfactant and flavor. The final mixture is heated to 60° C., processed through a mill and deaerated if necessary.

What is claimed is:

1. An anticalculus oral composition comprising:
   (a) a safe and effective amount of a chelator selected from the group consisting of polyacrylic acid polymers or copolymers, EDTA and mixtures thereof;
   (b) a safe and effective amount of a strontium ion source;
   (c) a safe and effective amount of a soluble pyrophosphate ion source;
   (d) a safe and effective amount of a fluoride ion source; and
   (e) a pharmaceutically acceptable carrier.

2. An oral composition according to claim 1 wherein (a) is a copolymer of acrylic acid and a monomer selected from the group consisting of methacrylic acid, 2-hydroxypropyl acrylate, 3-hydroxypropyl acrylate, 3-hydroxypropyl methacrylate, acrylamide and mixtures thereof.

3. An oral composition according to claim 1 wherein (a) is a polyacrylic acid polymer and is present at a level of from about 0.0003% to about 13%.

4. An oral composition according to claim 3 wherein the pyrophosphate ion source is selected from the group consisting of tetrasodium pyrophosphate, tetrapotassium pyrophosphate, disodium diacid pyrophosphate and mixtures thereof.

5. An oral composition according to claim 4 wherein the fluoride ion source is sodium fluoride.

6. An oral composition according to claim 5 wherein the pharmaceutically acceptable carrier is a toothpaste.

7. An oral composition according to claim 6 wherein the soluble strontium ion source is present at a level sufficient to provide from about 2 to about 10,000 ppm $Sr^{++}$.

8. An oral composition according to claim 6 wherein the polyacrylic acid polymer has a molecular weight of from about 1000 to about 1,200,000.

9. An oral composition according to claim 7 which also contains a silica dental abrasive.

10. An oral composition according to claim 8 wherein the soluble fluoride ion source is sodium fluoride present at a level sufficient to give from about 25 to about 5000 ppm $F^-$ in the composition.

11. An oral composition according to claim 1 wherein the pharmaceutically acceptable carrier is a mouthwash.

12. An oral composition according to claim 1 wherein the pharmaceutically acceptable carrier is a topical dental gel.

13. An oral composition according to claim 11 wherein (a) is a polyacrylic acid polymer and is present at a level of from about 0.0003% to about 13%.

14. An oral composition according to claim 13 wherein the soluble strontium ion source is present at a level sufficient to provide from about 2 to about 10,000 ppm $Sr^{++}$.

15. An oral composition according to claim 13 wherein the soluble fluoride ion source is sodium fluoride present at a level sufficient to give from about 25 to about 5000 ppm $F^-$.

16. An oral composition according to claim 1 wherein the pharmaceutically acceptable carrier is a lozenge.

17. An oral composition according to claim 1 wherein the pharmaceutically acceptable carrier is a chewing gum.

18. A method of reducing calculus on tooth enamel or dentin comprising applying a safe and effective amount of the composition according to claim 1 to the enamel/dentin.

19. A method according to claim 18 wherein the composition is in the form of a toothpaste.

20. A method according to claim 18 wherein the composition is in the form of a mouthwash.

21. A method according to claim 18 wherein the composition is in the form of a dental gel.

22. A method according to claim 18 wherein the composition contains sodium fluoride at a level sufficient to provide from about 25 to about 5000 ppm F.

* * * * *